(12) United States Patent
Venkata Ramana Rao et al.

(10) Patent No.: US 8,524,281 B2
(45) Date of Patent: Sep. 3, 2013

(54) COATED DRUG SPHEROIDS AND USES THEREOF FOR ELIMINATING OR REDUCING CONDITIONS SUCH AS EMESIS AND DIARRHEA

(75) Inventors: Sripriya Venkata Ramana Rao, Cedar Knolls, NJ (US); Syed Muzafar Shah, Delray Beach, FL (US); Christopher Richard Diorio, Campbell Hill, NY (US); Maja Vencl-Joncic, Highland Mills, NY (US); Eugene James Murphy, Newburgh, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/940,797

(22) Filed: Nov. 5, 2010

(65) Prior Publication Data
US 2011/0165257 A1 Jul. 7, 2011

Related U.S. Application Data

(60) Provisional application No. 61/259,387, filed on Nov. 9, 2009.

(51) Int. Cl.
*A61K 31/4709* (2006.01)
*A61K 35/00* (2006.01)

(52) U.S. Cl.
USPC ......... 424/494; 514/313; 514/291; 424/155.1

(58) Field of Classification Search
USPC .................. 424/494, 49, 155.1; 514/313
See application file for complete search history.

(56) References Cited

U.S. PATENT DOCUMENTS

| | | | |
|---|---|---|---|
| 6,002,008 A | 12/1999 | Wissner et al. | |
| 6,288,082 B1 | 9/2001 | Wissner et al. | |
| 6,297,258 B1 | 10/2001 | Wissner et al. | |
| 6,384,051 B1 | 5/2002 | Frost et al. | |
| 7,399,865 B2 | 7/2008 | Wissner et al. | |
| 2005/0025825 A1* | 2/2005 | Heasley et al. | 424/468 |
| 2005/0129761 A1* | 6/2005 | Venkata Ramana Rao et al. | 424/470 |
| 2006/0270669 A1* | 11/2006 | Chew et al. | 514/232.5 |
| 2007/0014859 A1* | 1/2007 | Shah et al. | 424/468 |
| 2007/0104721 A1* | 5/2007 | Moore et al. | 424/155.1 |
| 2009/0246198 A1* | 10/2009 | Dong et al. | 424/133.1 |
| 2009/0306101 A1* | 12/2009 | Solca et al. | 514/266.4 |

FOREIGN PATENT DOCUMENTS

| | | |
|---|---|---|
| EP | 1 854 463 | 11/2007 |
| WO | WO 2005/032513 | 4/2005 |
| WO | 2007/011619 A2 | 1/2007 |
| WO | WO2007/075794 | 7/2007 |
| WO | 2007/130438 A2 | 11/2007 |
| WO | WO 2007/130438 | 11/2007 |

OTHER PUBLICATIONS

Wong et al. Clin. Cancer Research 2009; 15 (7) Apr. 1, 2009 pp. 2552-2558.*
Bose et al. Expert Opin. Investig. Drugs (2009) 18 (11) pp. 1736-1751.*
Ilango et al. (International Jounal of Pharma and Bio Sciences. vol. 3; Issue 2; Apr.-Jun. 2012 pp. 55-62).*
International Search Report.
Boyce et al., "Requirement of pp60c-src expression for osteoclasts to form ruffled borders and resorb bone in mice," Clinical Investigation, 1992, 90, 1622-1627.
Bridges, "Current progress towards the development of tyrosine kinase inhibitors as anticancer agents," Expert Opinion on Emerging Drugs, 1998, 3, 279-292.
Folkman, "Angiogenesis in cancer, vascular, rheumatoid and other disease," Nature Medicine, 1995, 1, 27-31.
Mattsson et al., "Current concepts in restenosis following balloon angioplasty," Trends Cardiovasc. Med., 1995, 5, 200-204.
Raines et al., "Multiple growth factors are associated with lesions of atherosclerosis: specificity or redundancy?" Bioessays, 1996, 18, 271-282.
Shaw et al., "Pharmacological inhibition of restenosis: learning from experience," Trends Pharmacol. Sci. 1995, 16, 401-404.
Shawver et al., "Receptor tyrosine kinases as targets for inhibition of angiogenesis," Drug Discovery Today, 1997, 2, 50-63.
Traxler, "Tyrosine kinase inhibitors in cancer treatment (Part II)," Expert Opinion on Therapeutic Patents, 1998, 8, 1599-1625.
Wong et al., "A phase I study with neratinib (HKI-272), an irreversible pan ErbB receptor tyrosine kinase inhibitor, in patients with solid tumors," Clin. Cancer Res., 2009, 15, 2552-2558.
Ferron et al., "Oral bioavailability of pantoprazole suspended in sodium bicarbonate solution," Am. J. Health Syst. Pharm., 2003, 60, 1324-1329.
Hubber et al., "Pharmacokinetics of pantoprazole in man," Int. J. Clin. Pharmacol. Ther., 1996, 34, 185-194.
Hug et al, "A single-dose, crossover, placebo- and moxifloxacin-controlled study to assess the effects of neratinib (HKI-272) on cardiac repolarization in healthy adult subjects," Clin. Cancer Res. 2010, 16, 4016-4023.
Lu et al., "Preformulation stability study of the EGFR inhibitor HKI-272 (Neratinib) and mechanism of degradation," Drug Dev. Ind. Pharm., 2011.
Simon et al., "By 1023/SK&F 96022: biochemistry of a novel (H+ + K+)-ATPase inhibitor," Biochem. Pharmacol. 1990, 39, 1799-1806.

* cited by examiner

*Primary Examiner* — Anoop Singh
*Assistant Examiner* — Anna Falkowitz
(74) *Attorney, Agent, or Firm* — Jones Day

(57) ABSTRACT

The present invention provides an oral pharmaceutical formulation comprising coated spheroids of a kinase inhibitor such as neratinib, which formulation is designed to reduce or eliminate side effects associated with existing oral formulations of kinase inhibitors.

15 Claims, 2 Drawing Sheets

COATED DRUG SPHEROIDS AND USES THEREOF FOR ELIMINATING OR REDUCING CONDITIONS SUCH AS EMESIS AND DIARRHEA

CROSS REFERENCE TO RELATED APPLICATIONS

This application claims the benefit of U.S. Provisional Application Ser. No. 61/259,387, filed Nov. 9, 2009, which is incorporated by reference in its entirety.

FIELD OF THE INVENTION

The present invention relates to oral pharmaceutical formulations designed to reduce or eliminate adverse effects of drugs typically associated with side effects such as emesis and diarrhea. In particular, the invention is directed to oral pharmaceutical formulations comprising a drug such as (E)-N-(4-(3-chloro-4-(pyridin-2-ylmethoxy)phenylamino)-3-cyano-7-ethoxyquinolin-6-yl)-4-(dimethylamino) but-2-enamide, also known as neratinib, and a pharmaceutically acceptable salts thereof. Such formulations are provided as capsules and other dosage forms comprising spheroid particles having an enteric coating.

BACKGROUND OF THE INVENTION

Protein kinases are important in the transmission of biochemical signals, which initiate cell replication. Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration. Specific protein kinases have been implicated in adverse conditions including cancer [Traxler, P. M., *Exp. Opin. Ther. Patents*, 8, 1599 (1998); Bridges, A. J., *Emerging Drugs*, 3, 279 (1998)], restenosis [Mattsson, E., *Trends Cardiovas. Med.* 5, 200 (1995); Shaw, *Trends Pharmacol. Sci.* 16, 401 (1995)], atherosclerosis [Raines, E. W., *Bioessays*, 18, 271 (1996)], angiogenesis [Shawver, L. K., *Drug Discovery Today*, 2, 50 (1997); Folkman, J., *Nature Medicine*, 1, 27 (1995)] and osteoporosis [Boyce, *J. Clin. Invest.*, 90, 1622 (1992)]. Compounds capable of inhibiting the activity of receptor tyrosine kinases are known to be useful in the treatment of cancers, including but not limited to for example, non-small cell lung cancer (NSCLC), breast cancer, polycystic kidney disease, colonic polyps, and stroke in mammals.

Specific kinase inhibitors include compounds such as (E)-N-(4-(3-chloro-4-(pyridin-2-ylmethoxy)phenylamino)-3-cyano-7-ethoxyquinolin-6-yl)-4-(dimethylamino)but-2-enamide(neratinib); 4-[(2,4-dichloro-5-methoxyphenyl)amino]-6-methoxy-7-[3-(4-methylpiperazin-1-yl)propoxy]quinoline-3-carbonitrile (bosutinib); N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (sunitinib); 4-[(4-methylpiperazin-1-yl)methyl]-N-[4-methyl-3-[(4-pyridin-3-ylpyrimidin-2-yl)amino]phenyl] benzamide(imatinib); 4-[4-[[4-chloro-3-(trifluoromethyl) phenyl]carbamoylamino]phenoxy]-N-methyl-pyridine-2-carboxamide(sorafinib); N-(3-ethynyl phenyl)-6,7-bis(2-methoxyethoxy)quinazolin-4-amine(erlotinib); 4-methyl-N-[3-(4-methyl-1H-imidazol-1-yl)-5-(trifluoromethyl) phenyl]-3-[(4-pyridin-3-ylpyrimidin-2-yl)amino]benzamide (nilotinib); N-[3-chloro-4-[(3-fluorophenyl)methoxy] phenyl]-6-[5-[(2-methylsulfonylethylamino)methyl]-2-furyl]quinazolin-4-amine(laratinib); and others. Many kinase inhibitors are known to possess anti-tumor activity and are therefore useful for treating certain disease states, such as cancer, that result, at least in part, from deregulation of this receptor.

The kinase inhibitor neratinib is a weak base having low bioavailability and low solubility in both water and alcohol. Certain tablet formulations of neratinib, including the maleate salt form of neratinib, provide a limited amount of active (<40 weight percent) that can be loaded in the oral dosage form. It would be desirable to provide a formulation of neratinib maleate for oral administration that allowed larger amounts of active (>40 weight percent) in the oral dosage form.

Notably, diarrhea and nausea, often severe, are associated with existing oral formulations of kinase inhibitors such as tablet and capsule formulations of neratinib. Such oral formulations prepared by conventional methods have been used and are currently being used clinical trials of neratinib and have been associated with severe emesisi and diarrhea in those clinical trials. See, e.g., A Phase I Study with Neratinib (HKI-272), an Irreversible Pan ErbB Receptor Tyrosine Kinase Inhibitor, in Patients with Solid Tumors, Wong et al., Clinical Cancer Research Apr. 1, 2009 15, 2552. Similar side effects have been noted in connection with oral formulations of other kinase inhibitors. It would therefore be very desirable to provide formulations of neratinib and other kinase inhibitors for oral administration that reduces or eliminates side effects of emesis and diarrhea.

SUMMARY OF THE INVENTION

The invention relates to an improved drug-containing oral enteric-coated spheroid, typically in capsule form and typically comprising neratinib or another kinase inhibitor, developed to circumvent the adverse events (emesis, diarrhea, nausea) observed with current neratinib immediate release tablet formulations used currently in clinical studies. The adverse events observed with oral dosing of immediate release tablets are believed to generate locally from the GI system. Single ascending dose (SAD) and multiple ascending dose (MAD) studies conducted with the oral immediate release tablet formulation also indicate that the adverse events may be due to local effects. By avoiding the exposure of the drug in the stomach by means of an enteric-coated formulation it is believed that these adverse events may be avoided.

The present invention provides pharmaceutically acceptable solid compositions suitable for oral administration, said compositions comprising coated spheroids containing an active kinase inhibitor, for instance neratinib (including the maleate form of neratinib). In certain embodiments, capsules comprising spheroids of neratinib having an enteric coating are provided. In some embodiments, the invention provides a unit dosage form as a capsule, tablet, or other dosage form comprising coated spheroids of an active kinase inhibitor such as neratinib.

The present invention provides a pharmaceutically acceptable composition of (i) spheroid particles comprising: (a) 30-70 weight percent of an active ingredient selected from the group consisting of neratinib, bosutinib, sunitinib, imatinib, sorafinib, erlotinib, nilotinib and laratinib, and pharmaceutically acceptable salts thereof; (b) 20-30 weight percent of one or more fillers; (c) 5-15 weight percent of one or more wetting agents, said spheroid particles comprising 70-83 weight percent of the total composition; (ii) a sub-coating applied to said spheroid particles further comprising 1-4 weight percent of one or more pharmaceutically acceptable cellulose based polymers and (iii) 16-30 weight percent of one or more pharmaceutically acceptable polymers as an enteric coating applied to said sub-coating, said coating components (ii) and (iii) together comprising 17-30 weight percent of the total composition.

The present invention provides a pharmaceutically acceptable composition of (i) spheroid particles comprising: (a) 30-70 weight percent of neratinib or a pharmaceutically acceptable salt; (b) 20-30 weight percent of one or more fillers; (c) 5-15 weight percent of one or more wetting agents, said spheroid particles comprising 70-83 weight percent of the total composition; (ii) a sub-coating applied to said spheroid particles further comprising 1-4 weight percent of one or more pharmaceutically acceptable cellulose based polymers and (iii) 16-30 weight percent of one or more pharmaceutically acceptable polymers as an enteric coating applied to said sub-coating, said coating components (ii) and (iii) together comprising 17-30 weight percent of the total composition.

The present invention provides a pharmaceutically acceptable composition of (i) spheroid particles comprising: (a) 30-70 weight percent of the maleate form of neratinib; (b) 20-30 weight percent of microcrystalline cellulose; (c) 5-15 weight percent of a polysorbate, said spheroid particles comprising 70-83 weight percent of the total composition; (ii) a sub-coating applied to said spheroid particles further comprising 1-4 weight percent of hydroxypropylcellulose and (iii) 16-30 weight percent of a methacrylic acid polymer as an enteric coating applied to said sub-coating, said coating components (ii) and (iii) together comprising 17-30 weight percent of the total composition.

The present invention also provides methods for treating cancer while minimizing or eliminating side effects such as emesis and diarrhea comprising administering to a subject an effective amount of such spheroid-based pharmaceutically acceptable formulations comprising neratinib.

DETAILED DESCRIPTION OF CERTAIN EMBODIMENTS OF THE INVENTION

1. Definitions

Figure 1:
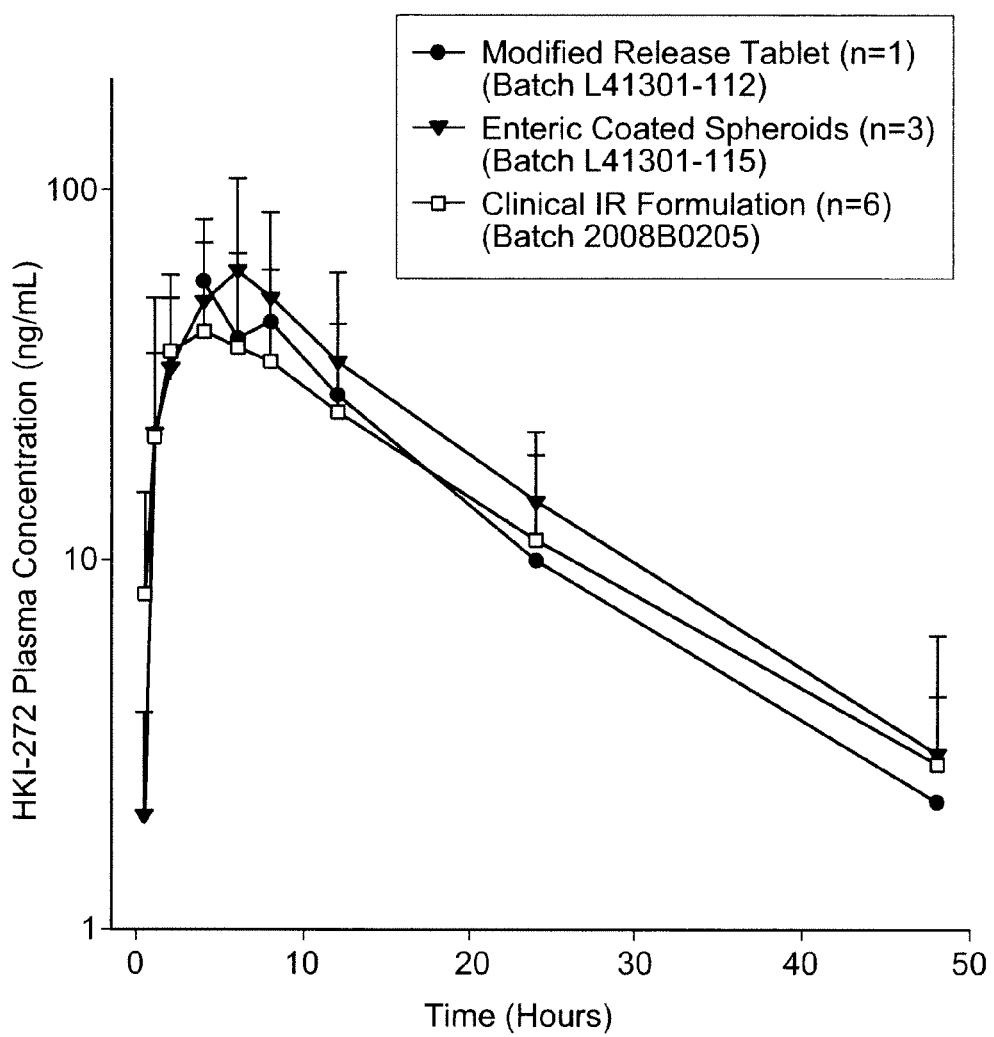
FIG. 1 summarizes pharmacokinetics of various neratinib maleate formulations in fasted male beagle dogs following oral administration.

As used herein, an "effective amount" of a compound or pharmaceutically acceptable composition can achieve a desired therapeutic and/or prophylactic effect. In some embodiments, an "effective amount" is at least a minimal amount of a compound, or composition containing a compound, which is sufficient for treating one or more symptoms of a disorder or condition associated with modulation of protein tyrosine kinases. In certain embodiments, an "effective amount" of a compound, or composition containing a compound, is sufficient for treating symptoms associated with, a disease associated with an aberrant tyrosine kinase receptor (e.g. cancer, including malignant and benign tumor growths).

The term "subject", as used herein, means a mammal and includes human and animal subjects, such as domestic animals (e.g., horses, dogs, cats, etc.).

The terms "suffer" or "suffering" as used herein refers to one or more conditions that a patient has been diagnosed with, or is suspected to have.

The terms "treat" or "treating," as used herein, refers to partially or completely alleviating, inhibiting, delaying onset of, preventing, ameliorating and/or relieving a disorder or condition, or one or more symptoms of the disorder or condition.

"Therapeutically active agent" or "active agent" refers to a substance, including a biologically active substance, that is useful for therapy (e.g., human therapy, veterinary therapy), including prophylactic and therapeutic treatment. Therapeutically active agents include organic molecules that are drug compounds, peptides, proteins, carbohydrates, monosaccharides, oligosaccharides, polysaccharides, nucleoprotein, mucoprotein, lipoprotein, synthetic polypeptide or protein, small molecules linked to a protein, glycoprotein, steroid, nucleic acid, DNA, RNA, nucleotide, nucleoside, oligonucleotides, antisense oligonucleotides, lipid, hormone, and vitamin. Therapeutically active agents include any substance used as a medicine for treatment, prevention, delay, reduction or amelioration of a disease, condition, or disorder. Among therapeutically active agents useful in the formulations of the present invention are opioid receptor antagonist compounds, opioid analgesic compounds, and the like. Further detailed description of compounds useful as therapeutically active agents is provided below. A therapeutically active agent includes a compound that increases the effect or effectiveness of a second compound, for example, by enhancing potency or reducing adverse effects of a second compound.

"Unit dosage form" as used herein refers to a physically discrete unit of inventive formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

2. Pharmaceutically Acceptable Compositions and Formulations

In certain embodiments, the present invention provides a pharmaceutically acceptable composition for oral administration comprising neratinib or pharmaceutically acceptable salts thereof. Neratinib and other and other compounds known to act as kinase inhibitors are disclosed, inter alia, in U.S. Pat. Nos. 6,002,008, 6,288,082, 6,297,258, 6,384,051 and 7,399,865. Neratinib has the chemical structure:

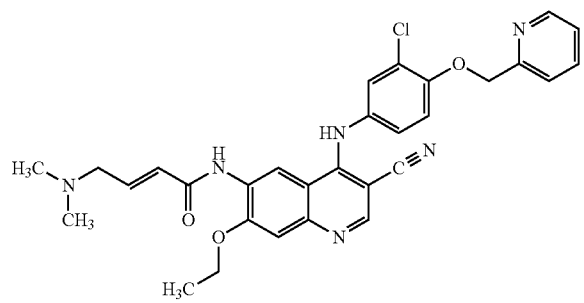 [SMILES: CCOc1cc2ncc(C#N)c(Nc3ccc(OCc4ccccn4)c(Cl)c3)c2cc1NC(=O)/C=C/CN(C)C]

and is isolated as a free base or prepared as a pharmaceutically acceptable salt, such as a maleate salt. Neratinib is a weak base with an intrinsic low solubility in water.

In certain embodiments, the invented formulation comprises spheroid particles of neratinib maleate having an enteric coating. Spheroid particles of neratinib maleate are prepared by extruding a mixture of neratinib maleate, plus one or more fillers and one or more wetting agents. One advantage of this technique is that a relatively small amounts of excipients are required to make the invented spheroid particles, as compared to formulations of neratinib maleate prepared by conventional wet granulation. A sub-coating comprising one or more cellulose based polymers is applied to the extruded spheroid particles of neratinib maleate and then an enteric coating comprising one or more pharmaceutically acceptable acrylic polymers is further applied to the sub-coated spheroid particles of neratinib maleate. Another advantage of the invention is that the coated particles of neratinib maleate have high loadings (40-70 weight percent, based on the weight of the formulation) of active ingredient neratinib maleate as compared to existing formulations and formulation techniques.

In certain embodiments, the formulations of the present invention include at least one enteric coating. Any enteric coating can be used in the present invention, including, but not limited to, solutions or dispersions of methacrylic acid and methacrylic ester copolymers, cellulose acetate phthalate, hydroxypropyl methylcellulose phthalate, hydroxypropyl methylcellulose acetate succinate, polyvinyl acetate phthalate, ethyl acrylate/methacrylic acid copolymers, methacrylic acid copolymer USNF Type A (Eudragit L™), Type B (Eudragit S™) Type C (Eudragit L 100-55™), Eudragit NE 30D, Eudragit E, Eudragit RL, Eudragit RS, cellulose acetate trimellitate, shellac and combinations thereof. Additionally, the enteric coating used in the formulations of the present invention can be formed as a single or multiple layers. The thickness of the coating can be readily determined by those skilled in the art, but must be sufficient to protect the formulation in the acidic environment of the stomach. The weight percent of the enteric coating, based on the total weight of the formulation is from 16-30 weight percent, including from 16-20 weight percent and about 17 weight percent. In one embodiment, the enteric coating comprises Acryl-Eze MP™ (Methacrylic acid plus other ingredients).

In certain embodiments, the formulations of the present invention include at least one sub-coating comprising one or more cellulose based polymers. Suitable cellulose based polymers include for example hydroxypropylmethylcellulose and hydroxypropylcellulose. The weight percent of the enteric coating, based on the total weight of the formulation is from 1-4 weight percent, including from 1-2 weight percent and about 1 weight percent. In one embodiment, the sub-coating comprises hydroxypropylmethylcellulose.

Suitable binders (also referred to as "diluents" and/or "fillers") are known in the art. For example, suitable binders and fillers include but are not limited to starch, dextrin, sucrose, Sorbitol, Sodium Saccharin, Acesulfame potassium, Xylitol, Aspartame, Mannitol, starch, PVP (polyvinyl pyrrolidone), low molecular weight HPC (hydroxypropyl cellulose), microcrystalline cellulose (MCC), low molecular weight HPMC (hydroxypropyl methylcellulose), low molecular weight carboxymethyl cellulose, ethylcellulose, alginates, gelatin, polyethylene oxide, acacia, dextrin, sucrose, magnesium aluminum silicate, and polymethacrylates. Fillers include agents selected from the group consisting of microcrystalline cellulose (MCC), starch, lactitol, lactose, a suitable inorganic calcium salt, sucrose, glucose, mannitol, silicic acid, or a combination thereof. In some embodiments, binders and fillers comprise from about 20 weight % to about 30 weight %, 25-30 weight %, including about 27.3 weight %, based upon total weight of the formulation. In some embodiments, the binder is one or more grades of microcrystalline cellulose, including but not limited to Avicel PH101™ and Avicel PH 102™.

Wetting agents are well known in the art and typically facilitate drug release and absorption. Exemplary wetting agents include poloxamer, polyoxyethylene ethers, polyoxyethylene sorbitan fatty acid esters polyoxyethylene fatty acid esters, polyethylene glycol fatty acid esters, polyoxyethylene hydrogenated castor oil, polyoxyethylene alkyl ether, polysorbates, cetyl alcohol, glycerol fatty acid esters (e.g., triacetin, glycerol monostearate, and the like), polyoxymethylene stearate, sodium lauryl sulfate, sorbitan fatty acid esters, sucrose fatty acid esters, benzalkonium chloride, polyethoxylated castor oil, and docusate sodium, and the like, and combinations thereof. In some embodiments, wetting agents include but are not limited to for example Polysorbate 80™, glycerin, Polysorbate 65™, polysorbate 60™ USP, Polysorbate 40™ USP, Polysorbate 20™ USP, Octoxynol-9, Nonoxynol-10™ USP, Poloxamer 235™, Poloxamer 188™ USP. In some embodiments, provided wetting agents comprise from about 5 weight % to about 15 weight %, about 7 weight % to about 10 weight %, or about 9 weight % based upon total weight of the formulation.

Addition of one or more preservatives may be particularly useful in compositions that include neratinib maleate, and may provide protection from degradation and/or from precipitation. Appropriate preservatives are known to those skilled in the art, and include any pharmaceutically acceptable preservative. Conventional preservatives include, but are not limited to sodium benzoate, Propyl parahydroxybenzoate, Sorbic acid, Propylparaben, Methylparaben, Butylated hydroxytoluene, Propionates, Potassium sorbate, Indinavir and combinations thereof. In some embodiments, provided preservatives comprise from about 0.05 weight %, to about 0.25 weight % or about 0.1%, based upon total weight of the formulation.

According to one embodiment, the active ingredient is formulated into a unit dosage form, well known to one of ordinary skill in the art. In certain embodiments, the present invention provides a formulation comprising a solid dosage form as capsules. In some embodiments, a unit dosage form contains 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1025 mg, 1050 mg, 1075 mg, 1100 mg, 1125 mg, 1150 mg, 1175 mg, 1200 mg, 1225 mg, 1250 mg, 1275 mg, 1300 mg, 1325 mg, 1350 mg, 1375 mg, 1400 mg, 1425 mg, 1450 mg, 1475 mg, 1500 mg of neratinib maleate. In some embodiments, a unit dosage form contains between 5 mg and 500 mg, inclusive, or between 10 mg and 450 mg, inclusive, of NERATINIB maleate. In some embodiments, a unit dosage form contains 40 mg, 80 mg, 100 mg, 120 mg, 240 mg, 360 mg, or 480 mg. In some embodiments, a unit dosage form contains more than 500 mg of neratinib maleate.

In some embodiments, the effective dosage of neratinib maleate employed may vary depending on the particular compound employed, the mode of administration and the severity of the condition being treated. However, in general, satisfactory results are obtained when the compounds of the invention are administered at a daily dosage of from about 0.5 to about 1000 mg/kg of body weight, optionally given in divided doses two to four times a day, or in sustained release form. The total daily dosage is projected to be from about 1 to 1000 mg, preferably from about 2 to 500 mg. Dosage forms suitable for internal use comprise from about 0.5 to 1000 mg of the active compound as coated spheroid particles. This dosage regimen may be adjusted to provide the optimal therapeutic response. For example, several divided doses may be administered daily or the dose may be proportionally reduced as indicated by the exigencies of the therapeutic situation.

For the treatment of cancer, the invented neratinib maleate formulations of this invention can be administered in combination with other anti-tumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, anti-metabolites such as 5-fluorouracil or hydroxyurea, DNA intercalators such as adriamycin or bleomycin, topoisomerase inhibitors such as etoposide or camptothecin, antiangiogenic agents such as angiostatin, and antiestrogens such as tamoxifen.

3. Combination Products and Combined Administration

In certain embodiments, inventive compositions, and formulations thereof, may be administered alone to treat one or more disorders as described herein, or alternatively may be administered in combination with (whether simultaneously or sequentially) one or more other active agents useful to treat one or more disorders as described herein. Thus, an inventive composition, or formulation thereof, can be administered concurrently with, prior to, or subsequent to, one or more active agents.

In certain embodiments, inventive compositions include one or more other active agents in addition to neratinib maleate. In some embodiments, inventive formulations comprise both another anticancer compound and neratinib maleate.

The amount of additional active agent(s) present in combination compositions of this invention will typically be no more than the amount that would normally be administered in a composition comprising that active agent as the only therapeutic agent. In certain embodiments of the present invention, the amount of additional active agent will range from about 50% to 100% of the amount normally present in a composition comprising that compound as the only therapeutic agent.

4. Uses and Kits of Inventive Compositions

Provided compositions, and formulations thereof, are also useful in treatment of conditions including cancers.

In still further embodiments, veterinary applications (e.g., treatment of domestic animals, e.g. horse, dogs, cats, etc.) of use of inventive compositions, and formulations thereof, are provided. Thus, use of provided formulations in veterinary applications analogous to those discussed above for human subjects is contemplated.

It will also be appreciated that inventive compositions, and formulations thereof, can be employed in combination therapies, that is, an inventive composition, or formulation thereof, can be administered concurrently with, prior to, or subsequent to, one or more other desired therapeutics or medical procedures. Particular combination therapies (therapeutics or procedures) to employ in a combination regimen will take into account compatibility of the desired therapeutics and/or procedures and the desired therapeutic effect to be achieved. It will also be appreciated that therapies employed may achieve a desired effect for the same disorder (for example, a formulation may be administered concurrently with another compound used to treat the same disorder), or they may achieve different effects (e.g., control of any adverse effects). As used herein, additional therapeutic compounds which are normally administered to treat or prevent a particular disease, or condition, are known as "appropriate for the disease, or condition, being treated".

In other embodiments, inventive compositions, and formulations thereof, and unit dose forms are useful in preparation of medicaments, including, but not limited to medicaments useful in the treatment of cancer.

Still further encompassed by the invention are pharmaceutical packs and/or kits comprising inventive compositions, and formulations thereof, and a container (e.g., a foil or plastic package, or other suitable container). Optionally instructions for use are additionally provided in such kits.

In order that the invention described herein may be more fully understood, the following examples are set forth. It should be understood that these examples are for illustrative purposes only and are not to be construed as limiting this invention in any manner.

All features of each of the aspects of the invention apply to all other aspects *mutatis mutandis*.

EXAMPLES

Example 1

Preparation of Neratinib Maleate as Enterically Coated Spheroid Particles

Step 1. Preparation of Neratinib Maleate Spheroid Particles (Using Extrusion/Spheronization Method):

Neratinib maleate (140 g) and Avicel PH 101 (60 g) were bag blended in a plastic container for three minutes and transferred into a Hobart mixer. The contents were dry mixed for 30 sec. Polysorbate-80™ solution (0.25% w/w) was prepared. Then 100 g of this solution was added to the Hobart mixer in small increments while continuously mixing the contents. A wet mass was obtained. The wet mass was extruded through a Nica Extruder set up at a Feeder speed of 40 rpm and agitator speed of 80 rpm. Small extrudates were obtained. The extrudates were then spheronized in Nica Spheronizer for 3 minutes set at a speed of 900 rpm. The spheroids were tray dried to final moisture content of 2.5% (range: 2-3%). The spheroids were sieved to a cut of 18-mesh (1000 micron) and 35-mesh (500 micron) screen. The screened spheroid material (remaining on the 35-mesh screen) was used in the sub coating step.

Step 2. Sub-Coating Neratinib Maleate Spheroid Particles with Hydroxypropylmethylcellulose (HMPC):

The spheroids were loaded into a fluid bed processor with a bottom Wuster spray. Prepared 15% w/w solution of hydroxypropylmethylcellulose, 3 cps. Applied the hydroxypropylmethylcellulose (HMPC) solution using an inlet temperature of 50°±5° C. The process was carried out until a weight gain of 1.2% (range: 1-4%). The spheroids were then dried in the fluid bed for 15 minutes.

Step 3. Enteric Coating of Sub-Coated Neratinib Maleate Spheroid Particles with Acryl-Eze MP:

The HMPC coated spheroids were loaded into a fluid bed processor with a bottom Wuster spray. Then Acryl-Eze MP™ solution with 20% solids content was prepared and the enteric coating solution was applied using an inlet temperature of 32°±3° C. The process was carried out until a weight gain of 16.9% (range: 16-30%) was obtained. The enteric-coated spheroids were dried in the fluid bed for 15 minutes. Then the spheroids were stored in a plastic container.

Step 4. Capsule Preparation of Coated Neratinib Maleate Spheroid Particles:

The enteric-coated spheroids are filled in HPMC capsule according to the strength needed. The potency of the enteric-coated spheroids determined the quantity to be filled in per capsule.

Example 2

Exemplary Neratinib Maleate Formulation

| Ingredients | Enteric Coated Spheroids in Capsule | |
|---|---|---|
| | % W/W Composition | Range |
| Uncoated Spheroids | | |
| Neratinib maleate | 63.64 (equivalent to 52.63 free base) | — |
| Microcrystalline Cellulose (Avicel PH 101) | 27.27 | 20-30% |
| Polysorbate-80 | 9.09 | 5-15% |
| Total | 100 | — |
| Sub-Coating | | |
| Hypromellose, 3 cps | 1.2% weight gain | 1-4% |
| Enteric Coating | | |
| Acryl-Eze MP (Methacrylic acid plus other ingredients) | 16.9% weight gain | 16-30% |

Example 3

Pharmokinetic Evaluation of Neratinib Maleate Coated Spheroid Formulation

The invented neratinib maleate formulation and two other neratinib maleate formulations for oral administration were evaluated in six fasted male beagle dogs (10.2-15.7 kg), as summarized in Table 1 and FIG. 1.

Blood samples were drawn at 0 (predose), 0.5, 1, 2, 4, 6, 8, 12, 24 and 48 hours after dosing, plasma was separated and assayed for neratinib maleate content. Individual dog plasma neratinib maleate concentration-time profiles following oral tablet dosing were subjected to non-compartmental pharmacokinetic analyses (WinNonlin, Model 200). The following pharmacokinetic parameters were determined for each dog, and descriptive statistics were calculated: AUC, $C_{max}$, $t_{max}$ and $t_{1/2}$. Dose normalized AUC values were calculated by normalizing the dose to individual animal's body weight. High variability was observed in neratinib maleate $C_{max}$ and AUC values following oral administration. neratinib maleate $C_{max}$ and AUC values from the enteric coated spheroids are qualitatively similar to those observed from other tablet formulations of neratinib maleate used in clinical trials.

The oral bioavailability of neratinib maleate enteric-coated spheroids in capsule formulation (21%) is slightly higher than other HKI maleate tablet formulations (17%) currently used in the clinic. In addition to the increased lag time of the enteric-coated spheroid formulation, the $C_{max}$ and $T_{max}$ is significantly higher as compared to such neratinib maleate tablet formulations.

Example 4

Comparison of Adverse Effects for Neratinib Maleate Formulations

The inventive neratinib maleate formulation in the form of enteric-coated spheroid capsules circumvents adverse events (emesis, diarrhea, nausea) as compared to wet granulated tablets of a clinical neratinib maleate tablet formulation. Adverse events in the study summarized in Example 3 are presented in Table 2.

TABLE 2

Occurrence of GI Tract Related Effects After Single IV or Oral Administration of neratinib maleate Tablets to Fasted Male Beagle Dogs

| Treatment | SAN | Observation | Approx. time of Occurrence |
|---|---|---|---|
| neratinib maleate tablet | 6 | Emesis | ~6 hr post dose |
| formulation used | 6 | Emesis | ~8 hr post dose |

TABLE 1

Individual and Mean (±SD) Plasma neratinib maleate Formulation Pharmacokinetic Parameters in Fasted Male Beagle Dogs Following a Single Oral Dose (80 mg)

| Formulation (Batch) | SAN | Dose (mg/kg) | $C_{max}$ (ng/mL) | $t_{max}$ (hr) | $t_{lag}$ (hr) | $AUC_{0-t}$[a] (hr * ng/mL) | $AUC_{0-\infty}$ (ng * hr/mL) | $t_{1/2}$ (hr) | $C_{max}$/ Dose | $AUC_{0-t}$/ Dose |
|---|---|---|---|---|---|---|---|---|---|---|
| Neratinib maleate enteric coated spheroids | 4 | 7.62 | 102 | 6.0 | 0.5 | 1543 | 1605 | 9.8 | 13.3 | 203 |
| | 5 | 6.61 | 69.6 | 6.0 | 0.0 | 1154 | 1187 | 9.2 | 10.5 | 175 |
| | 6 | 5.11 | 16.2 | 2.0 | 0.0 | 326 | NC | NC | 3.17 | 64.0 |
| | Mean ± SD | 6.44 ± 1.27 | 62.5 ± 43.2 | 4.7 ± 2.3 | 0.2 ± 0.3 | 1008 ± 622 | 1396 (n = 2) | 9.5 (n = 2) | 9.01 ± 5.25 | 147 ± 73.3 |
| Neratinib maleate wet granulated tablets | 1 | 7.77 | 15.0 | 2.0 | 0.5 | 434 | NC | NC | 1.93 | 55.9 |
| | 2 | 6.35 | 56.6 | 6.0 | 0.0 | 1404 | 1598 | 14.9[b] | 8.91 | 221 |
| | 3 | 5.56 | 10.1 | 2.0 | 0.0 | 132 | 155 | 8.4 | 1.81 | 23.8 |
| | 4 | 7.41 | 75.2 | 4.0 | 0.0 | 1029 | 1059 | 9.4 | 10.1 | 139 |
| | 5 | 6.67 | 26.9 | 1.0 | 0.0 | 339 | NC | NC | 4.03 | 50.8 |
| | 6 | 5.13 | 80.5 | 6.0 | 0.0 | 1213 | 1270 | 10.9 | 15.7 | 236 |
| | Mean ± SD | 6.48 ± 1.02 | 44.0 ± 30.8 | 3.5 ± 2.2 | 0.1 ± 0.2 | 759 ± 523 | 1021 ± 618 | 10.9 ± 2.8 | 7.09 ± 5.49 | 121 ± 92.0 |

[a]Value represents area until the last observed concentration-time point

TABLE 2-continued

Occurrence of GI Tract Related Effects After
Single IV or Oral Administration of neratinib
maleate Tablets to Fasted Male Beagle Dogs

| Treatment | SAN | Observation | Approx. time of Occurrence |
|---|---|---|---|
| in clinical trials | 4 | Watery feces | ~8 hrs post dose |
| | 5 | Watery feces | ~12 hrs post dose |

Emesis/watery feces were observed for the wet granulated neratinib maleate tablet formulation whereas administering the invented neratinib maleate formulation resulted in no occurrence of emesis/watery feces.

Example 5

Figure 2:
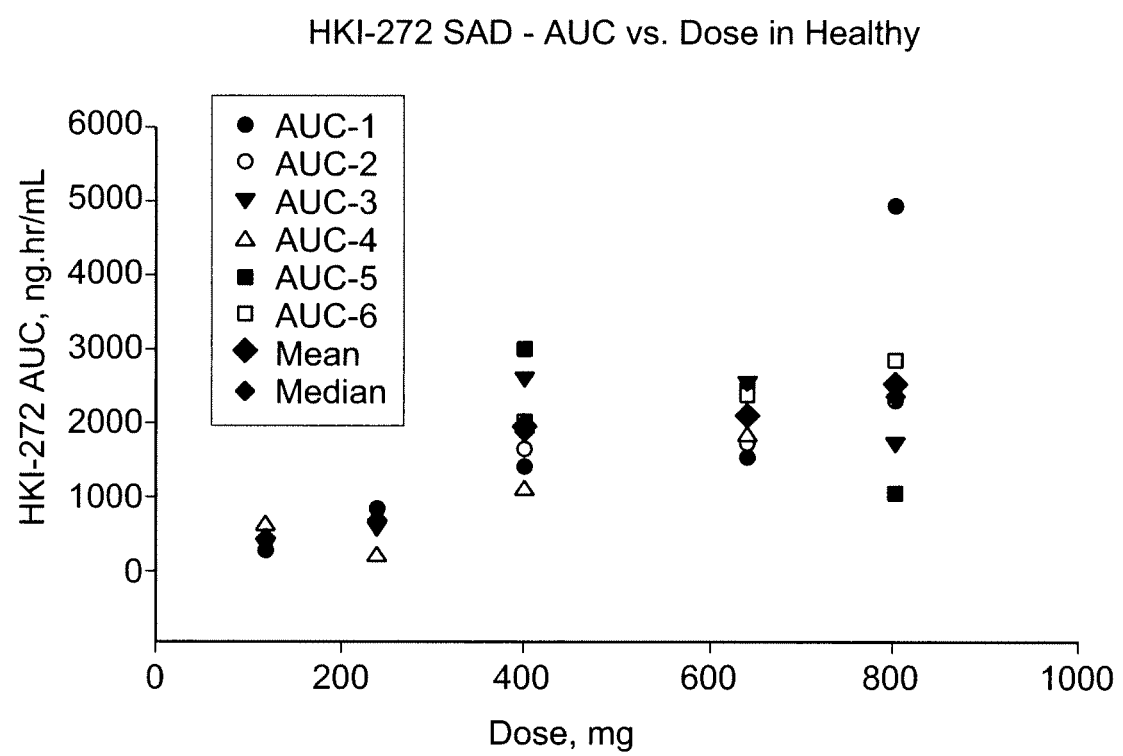
FIG. 2 summarizes a comparison of the frequency and severity of gastrointestinal adverse events in single ascending dosage study of neratinib maleate formulation in healthy subjects.

Summary of Gastrointestinal Adverse Events Observed in Single Dose Neratinib Maleate Clinical Studies of Healthy Subjects In a clinical study, 192 healthy subjects were given five single doses of neratinib maleate. Adverse events were observed and classified as follows:
  Grade 1 gastrointestinal adverse events (GI AEs) ~25%-40%
  Grade 2 gastrointestinal adverse events (GI AEs) ~15%
  Grade 1 and 2 gastrointestinal adverse events predominated as the adverse events observed in clinical studies of healthy subjects. In further studies, healthy subject data at two different single dose levels (400 mg and 800 mg) suggests neratinib produces gastrointestinal adverse events by local effects, as summarized in FIG. 2. In fact, the frequency and severity of GI AEs between 400 mg and 800 mg fasted was most significantly impacted by dose (and not Cmax or AUC), with a leveling of the adverse events observed. The results indicated that adverse events generate locally from the GI system.

Example 6

Gastrointestinal Adverse Events Observed in Multiple Dose Neratinib Maleate Clinical Studies of Cancer Patients Six different multiple dose clinical studies using neratinib maleate (single agent and combination) in cancer patients (>400 patients) also indicated that gastrointestinal adverse events predominated as the adverse events observed in clinical studies of cancer patients. Adverse events in clinical studies of cancer patients were observed and classified as follows:
  Nausea, Vomiting, Diarrhea, Dehydration, Anorexia (~95%)
  Asthenia, Fatigue (~30-60%)
  Rash (~20-25%)
  Elevated ALT, AST (<10%)

Example 7

Effect of Concurrent Administration of Ketoconazole on GI Tolerability

Exposure studies were performed to determine if gastrointestinal tolerability is related to systemic exposure of neratinib maleate. The results indicated that GI tolerability (diarrhea) is not related to systemic exposure.

| Parameter [Geo mean] | 240 mg Neratinib | 240 mg Neratinib + Ketoconazole |
|---|---|---|
| Cmax (ng/ml) | 55.32 [51.5] | 201 [164] |
| AUC t (hr*ng/ml) | 835 [727] | 4355 [3527] |
| AUC∞ (hr*ng/ml) | 903 [802] | 4660 [3796] |

Subjects Reporting GI AEs

| | % | % |
|---|---|---|
| GI Disorders | 31.8 | 30.4 |

Example 8

Extended Release Neratinib Maleate Formulation

| Ingredients | Modified release Spheroids in Capsule % W/W Composition |
|---|---|
| Uncoated Spheroids | |
| Neratinib maleate | 63.64 (equivalent to 52.63 free base) |
| Microcrystalline Cellulose (Avicel PH 101) | 27.27 |
| Polysorbate-80 | 9.09 |
| Total | 100 |
| Sub-Coating | |
| Hypromellose, 3 cps | 1.2% weight gain |
| Modified Release Coating | |
| Surelease (ethylcellulose aqueous dispersion) | 10% weight gain |

We claim:
1. A pharmaceutically acceptable composition of (i) spheroid particles comprising: (a) 30-70 weight percent of (E)-N-(4-(3-chloro-4-(pyridin-2-ylmethoxy)phenylamino)-3-cyano-7-ethoxyquinolin-6-yl)-4-(dimethylamino)but-2-enamide or a pharmaceutically acceptable salt thereof as an active ingredient; (b) 20-30 weight percent of one or more fillers; and (c) 5-15 weight percent of one or more wetting agents, said spheroid particles comprising 70-83 weight percent of the total composition; (ii) a sub-coating applied to said spheroid particles further comprising 1-4 weight percent of one or more pharmaceutically acceptable cellulose based polymers and (iii) 16-30 weight percent of one or more pharmaceutically acceptable polymers as an enteric coating applied to said sub-coating, said coating components (ii) and (iii) comprising 17-30 weight percent of the total composition;
  wherein the enteric coated composition has an $AUC/C_{max}$ ratio that is the same as or less than the $AUC/C_{max}$ ratio of an immediate release formulation of the active ingredient without enteric coating.

2. A pharmaceutically acceptable composition of (i) spheroid particles comprising: (a) 30-70 weight percent of (E)-N-(4-(3-chloro-4-(pyridin-2-ylmethoxy)phenylamino)-3-cyano-7-ethoxyquinolin-6-yl)-4-(dimethylamino)but-2-enamide maleate as an active ingredient; (b) 20-30 weight percent of microcrystalline cellulose; and (c) 5-15 weight percent of a polysorbate, said spheroid particles comprising 70-84 weight percent of the total composition; (ii) a sub-coating applied to said spheroid particles further comprising 1-4 weight percent of hydroxypropylcellulose and (iii) 16-30 weight percent of a methacrylic acid polymer as an enteric coating applied to said sub-coating, said coating components (ii) and (iii) comprising 16-30 weight percent of the total composition; wherein the enteric coated composition has an $AUC/C_{max}$ ratio that is the same as or less than the $AUC/C_{max}$ ratio of an immediate release formulation of the active ingredient without enteric coating.

3. The composition according to claim 2, wherein the weight percent of (E)-N-(4-(3-chloro-4-(pyridin-2-ylmethoxy)phenylamino)-3-cyano-7-ethoxyquinolin-6-yl)-4-(dimethylamino)but-2-enamide maleate is from 55-65.

4. The composition according to claim 2, wherein the weight percent of (E)-N-(4-(3-chloro-4-(pyridin-2-ylmethoxy)phenylamino)-3-cyano-7-ethoxyquinolin-6-yl)-4-(dimethylamino)but-2-enamide maleate is 63.6.

5. The composition according to claim 2, wherein the weight percent of the polysorbate is from 7-10.

6. The composition according to claim 2, wherein the weight percent of the polysorbate is about 9.

7. The composition according to claim 2, wherein the weight percent of the microcrystalline cellulose is about 27.

8. The composition according to claim 2, in the form of an oral dosage of 40 mg.

9. The composition according to claim 2, in the form of an oral dosage of 80 mg.

10. The composition according to claim 2, in the form of an oral dosage of 240 mg.

11. A pharmaceutically acceptable composition of (i) spheroid particles comprising: (a) 30-70 weight percent of an active ingredient selected from the group consisting of neratinib, bosutinib, erlotinib, sutent, tykerb, a 4-amino-3-cyanoquinoline compound and pharmaceutically acceptable salts thereof; (b) 20-30 weight percent of one or more fillers; and (c) 5-15 weight percent of one or more wetting agents, said spheroid particles comprising 70-83 weight percent of the total composition; (ii) a sub-coating applied to said spheroid particles further comprising 1-4 weight percent of one or more pharmaceutically acceptable cellulose based polymers and (iii) 16-30 weight percent of one or more pharmaceutically acceptable polymers as an enteric coating applied to said sub-coating, said coating components (ii) and (iii) comprising 17-30 weight percent of the total composition;

wherein the enteric coated composition has an $AUC/C_{max}$ ratio that is the same as or less than the $AUC/C_{max}$ ratio of an immediate release formulation of the active ingredient without enteric coating.

12. The composition according to claim 2, wherein the composition is to reduce or eliminate a gastrointestinal side effect of (E)-N-(4-(3-chloro-4-(pyridin-2-ylmethoxy)phenylamino)-3-cyano-7-ethoxyquinolin-6-yl)-4-(dimethylamino)but-2-enamide maleate.

13. The composition according to claim 12, wherein the gastrointestinal side effect is emesis.

14. The composition according to claim 12, wherein the gastrointestinal side effect is diarrhea.

15. The composition according to claim 12, wherein the gastrointestinal side effect is nausea.

* * * * *